United States Patent [19]
Chung et al.

[11] Patent Number: 6,159,467
[45] Date of Patent: *Dec. 12, 2000

[54] IN VIVO SUPPRESSION OF OSTEOSARCOMA PULMONARY METASTASIS WITH INTRAVENOUS OSTEOCALCIN PROMOTER-BASED TOXIC GENE THERAPY

[75] Inventors: Leland W. K. Chung, Lovingston; Chinghai Kao, Charlottesville; Robert A. Sikes, Charlottesville; Song-Chu Ko, Charlottesville, all of Va.; Jun Cheon, Sung Bu ku Sol, Rep. of Korea

[73] Assignee: The University of Virginia Patent Foundation, Charlottesville, Va.

[*] Notice: This patent is subject to a terminal disclaimer.

[21] Appl. No.: 09/010,114

[22] Filed: Jan. 21, 1998

Related U.S. Application Data

[63] Continuation-in-part of application No. 08/785,088, Jan. 21, 1997, Pat. No. 5,772,993.
[51] Int. Cl.$^7$ .......................... A61K 48/00; A01N 63/00; C12P 21/04; C12N 15/00
[52] U.S. Cl. .......................... 424/93.6; 424/9.2; 435/71.2; 435/320.1; 514/44
[58] Field of Search .................................. 424/9.2, 93.6; 435/71.2, 320.1; 514/44

[56] References Cited

U.S. PATENT DOCUMENTS 5,631,236  5/1997  Woo et al. .

FOREIGN PATENT DOCUMENTS

WO9701358  1/1997  WIPO .

OTHER PUBLICATIONS

Human Gene Therapy, 7(4) 463–70, Mar. 1, 1996, Su. et al., Selective Killing of AFP–Positive Hepatocellular Carcinoma Cells by Adeno–Associated Virus Transfer of the Herpes Simplex Virus Thymidine Kinase Gene.
Cancer Research, 56(20) 4614–9, Oct. 15, 1996, Ko. et al., Osteocalcin Promoter–Based Toxic Gene Therapy for the Treatmetn of Osteosarcoma in Experimental Models.

*Primary Examiner*—Geetha P. Bansal
*Attorney, Agent, or Firm*—Pennie & Edmonds LLP

[57] ABSTRACT

A therapeutic agent based on a recombinant adenovirus which employs an osteocalcin promoter for the expression of thymidine kinase can be administered intravascularly to treat metastatic cancer, including osteosarcoma, breast cancer, prostate cancer, ocular melanoma or brain cancer. Systemic administration of this agent provides a preferred route over previous disclosure of local direct administration. The same therapeutic agent can be effectively employed in the treatment of benign conditions, including benign prostatic hypertrophy and arteriosclerosis.

10 Claims, 7 Drawing Sheets

IN VIVO SUPPRESSION OF OSTEOSARCOMA PULMONARY METASTASIS WITH INTRAVENOUS OSTEOCALCIN PROMOTER-BASED TOXIC GENE THERAPY

This application is a continuation-in-part of U.S. patent application 08/785,088, filed Jan. 21, 1997, now U.S. Pat. No. 5,772,993. The entire content of the parent application is incorporated herein-by-reference.

BACKGROUND OF THE INVENTION

1. Field of the Invention

This invention pertains to the systemic administration of an active agent, a recombinant gene comprising an adenovirus (Ad) which contains an osteocalcin promoter (OC) which drives the expression of thymidine kinase (TK). The agent itself is fully disclosed in the parent application. This invention pertains to the discovery that Ad-OC-TK may be administered systemically, both to treat tumors, and to treat certain benign conditions such as benign prostatic hypertrophy and certain forms of arteriosclerosis.

2. Background of Related Work

Toxic gene therapy for the treatment of cancer continues to gain prominence in basic research, but remains limited in clinical application because of an inability to deliver the toxic gene to the tumor cells with specificity. Many vectors (e.g. retroviruses, retroviral producing cells, adenoviruses, liposomes, and others) can deliver genes (therapeutic or toxic) to target cells. Localized delivery and restricted gene expression to the primary tumor have been accomplished via direct injection of therapeutic viruses in animal models[1-4] and clinical trails.[5,6] This approach is not feasible for the treatment of metastatic disease because of the presence of multiple lesions that would each require separate injection and manipulation. Therefore, alternative approaches to the treatment of metastatic disease with gene therapy must be developed.

Systemic delivery of therapeutic genes is attractive for targeting metastatic disease, pulmonary metastases in particular. Because the pulmonary vascular system would be the first encountered, the adenovirus would be trapped in the lung parenchyma, allowing for higher infectivity. Lesoon-Wood et al.[7] reported the systemic delivery of wild type p53 complexed with liposomes, targeting the p53 mutated breast cancer cell line (MDA-MB435), inhibiting primary tumor growth by 60%, and decreasing pulmonary metastases in nude mice. Vile et al.[8] demonstrated inhibition of B-16 melanoma pulmonary metastases in syngeneic immunocompetent mice by a systemic delivery of retrovirus using a tyrosinase promoter to drive the expression of the toxic gene thymidine kinase (TK) gene.

Compared to liposome or retrovirus, adenovirus has several advantages in a systemic delivery strategy, such as its high infectivity in vivo and production techniques that can achieve high viral titers. However, Brand et al.[9] recently reported that systemic administration of adenovirus containing TK under the control of a universal promoter (CMV) supplemented with ganciclovir treatment induced severe hepatotoxic effects. This study suggested that restriction of toxic gene (TK) expression by tissue specific promoter may be necessary prior to the consideration of systemic adenoviral vector delivery. Moreover, the tissue-specific promoter should limit the toxic gene expression in normal tissues so it can be applied in higher doses than the universal promoter-based toxic gene therapy for more effective treatment of metastatic diseases.

To study the potential therapeutic efficacy of systemic cancer gene therapy for the treatment of pulmonary metastases, osteosarcoma is an attractive model because a significant number of these patients eventually develop lung metastasis. Initially, surgical resection of the primary lesion and adjunctive chemotherapy are the mainstay of today's therapy. For the 20% that present with metastatic disease, 80% will require additional therapy for relapse; while of the 80% that present with local disease, 35% will require additional therapy for relapse after surgery and adjunctive chemotherapy.[10] Therefore, 44% of patients diagnosed with osteosarcoma will fail conventional first line therapy. Patients developing recurrent disease usually have a poor prognosis, dying within one year of the development of metastatic disease.[11-14] New therapeutic approaches that can be applied either separately or in conjunction with current modalities in treating osteosarcoma pulmonary metastases are needed.

The osteocalcin promoter (OC) has been shown to be highly effective in directing the transcription of reporter genes in both rat and human osteosarcoma cell lines.[4,15] In parent application U.S. Ser. No. 08/785,088 (now U.S. Pat. No. 5,772,993) and concurrent publications it was shown that a recombinant adenovirus containing TK gene under the control of OC promoter, when supplemented with a prodrug ACV, could suppress osteosarcoma growth through intralesional injection in both rat and human osteosarcoma models.[1,4]

Osteosarcoma, a bone cancer occurring primarily in teenagers and young adults, affects approximately 2100 individuals yearly in the United States (Boring, C. C., Squires, T. S., Tong, T., and Montgomery. S. Cancer statistics, 1994, CA Cancer J. Clin., 44;7–26, 1994). This malignancy accounts for as many as 5% of all childhood malignancies and 60% of all malignant childhood bone tumors (Hudson, M., Jaffe, M. R., and Jaffe, N. Pediatric osteosarcoma: therapeutic strategies, results, and prognostic actors derived from a 10 10-year experience. J. Clin. Oncol., 8: 1988–1997, 1990). Despite radical surgical resection of the primary tumor and aggressive adjuvant chemotherapy, the overall 2-year metastasis-free survival rate approaches only 66%. More than 30% of patients with this disease develop lung metastasis within the first year (Link, M. P., Goorin, A. M., Mixer, A. W., Link, M. P., Goorin, A. M., Miser, A. W., Green, A. A., Pratt, C. H., Belasco, J. B., Pritchard, J., Malpas, J. S., Baker, A. R., Kirkpatrick, J. A., Ayala, A. O., Schuster, J. J., Abelson, H. T., Simone, J. V., and Vietti, T. J. The effect of adjuvant chemotherapy on relapse-free survival in patients with osteosarcoma of the extremity. N. Engl. J. Med, 314: 1600–1602, 1991. Goorin, A. M., Perez-Atayde, A., Gebbhardt, M., et al. Weekly high-dose methotrexate and doxorubicin for osteosarcoma: the Dunn-Farber Cancer Institute/The Children's Hospital-Study III. J. Clin. Oncol., 5: 1178–1184, 1987). The survival rate among those affected with osteosarcoma has not changed significantly over the past 10 years, despite changes in adjuvant chemotherapy, Kane, M. J. Chemotherapy of advanced soft tissue and osteosarcoma. Semin. Oncol., 16:297–304, 1989.

The concept of delivery and expression of therapeutic toxic genes to tumor cells through the use of tissue-specific promoters has been well recognized. This approach could decrease the toxic effect of therapeutic genes on neighboring normal cells when virus-mediated gene delivery results in the infection of the normal cells. Examples include the uses of the albumin or α-fetoprotein promoter to target hepatoma cells (Kuriyama, S., Yoshikawa, M., Ishizaka, S., Taujli, T., Ikenaka, K., Kagawa, T., Morita, N., and Mikoshiba, K. A.

potential approach for gene therapy targeting hepatoma using a liver-specific promoter on a retroviral vector, Cell Struct. Punct., 16: 503–510, 1991), the bone morphogenic protein promoter for brain to target glioma cells (Shimizu, K. Selective gene therapy of malignant glioma using brain-specific promoters; its efficacy and basic investigation, Nippon Rinsbo, 52: 3053–3058, 1994), the tyrosinase promoter to kill melanoma cells (Vile, R. G., Nelson, J. A., Castleden, S., Chong, H., and Hart, I. R. Systemic gene therapy of murine melanoma using tissue specific expression of the HSVtk gene involves an immune component. Cancer Res., 54:6228–6234, 1994), and the carcinoembryonic antigen promoter for gastric carcinoma cells (Tanaka, T., Kanai. F., Okabe, S., Yoshida, Y., Wakimoto, H., Hamada, H., Shiratori, Y., Lan, K-H., Ishitobi, M., and Omata, M. Adenovirus-mediated prodrug gene therapy for carcinoembryonic antigen-producing human gastric carcinoma cells in vitro. Cancer Res., 46: 1341–1345, 1996). To date, the best studied therapeutic gene is herpes simplex virus TK gene. Herpes simplex virus-TK converts the pro-drug ACV to a phosphorylated form that is cytotoxic to dividing cells (Moolten, F. L., Tumor chemosensitivity conferred by inserted herpes thymidine kinase genes; paradigm for a prospective cancer control strategy. Cancer Res., 46:5276–5281, 1986). Critical to successful results is the "bystander" effect, which confers cytotoxicity on neighboring nontransduced cells; effective tumor cell kill can be achieved without the delivery to and expression of suicide genes in every tumor cell in vivo. This approach has been demonstrated recently to be efficacious in causing regression of many solid tumors, including metastatic colon carcinoma in the rat liver, (Chen, S. II., Chen, X.H.L., Wang, Y., Kosal, K. E., Finegold, J. J., Rich, S. S., and Woo, S.L.C., Combination gene therapy for liver metastasis of colon carcinoma in vivo. Proc. Natl.

Acad. Sci. USA. 92:2577–2581, 1995), gastric carcinoma, (Tanaka, T., Kanai. F., Okabe, S., Yoshida, Y., Wakimoto, H., Hamada, H., Shiratori, Y., Lan, K-H., Ishitobi, M., and Omata, M. Adenovirus-mediated prodrug gene therapy for carcinoembryonic antigenproducing human gastric carcinoma cells in vitro. Cancer Res., 46: 1341–1345, 1996), and malignant mesothelioma (Smythe, W. R., Hwang, B. S., Elshami, A. A., Amin, K. M., Eck, S., Davidson, B. L., Wilson, J. M., Kaiser, L. R., and Albelda, S. M. Treatment of experimental human mesothelioma using adenovirus transfer of the herpes simplex thymidine kinase gene. Ann. Surg., 222:78–86, 1995).

Osteocalcin (OC), a noncollagenous Gla protein produced specifically in osteoblasts, is synthesized, secreted, and deposited at the time of bone mineralization (Price, P. A. Vitamin-K dependent formation of bone GLA protein (onteocalcin) and its function. Vitam. Horm., 42:65–108, 1985). A recent study showed that immunohistochemical staining of OC as positive in primary osteoblastic osteosarcoma and chondroblastic osteosarcoma specimens as well as in five of seven fibroblastic osteosarcomas (Park, Y. K., Yung, M. H., Kim, Y. W., and Park, H. R. Osteocalcin expression in primary bone tumors: in situ hybridization and immunohistochemical study. J. Korean Med. Sci., 10:268–273, 1995). In addition, OC activity was detected in a wide spectrum of human tumors. This is consistent with the clinical observations that many human tumors exhibited calcification characteristics both in the primary and at distant metastases.

Because of the poor response rate of previously treated patients with relapsed osteosarcoma to second-line chemotherapy and the fact that many human solid tumors failed to respond to conventional chemotherapy and radiation therapy, it is important to develop new therapeutic approaches that can be applied either separately or in conjunction with current treatment modalities.

SUMMARY OF THE INVENTION

Pulmonary metastasis is the main cause of death of patients with several types of cancer, including osteosarcoma, renal cell carcinoma, malignant melanoma, and breast cancer. This application demonstrates the efficacy of the treatment of osteosarcoma pulmonary metastases with a systemic delivery route of Ad-OC-TK supplemented with ACV. We established osteosarcoma lung metastases in nude mice by intravenous injection of rat osteosarcoma cells, ROS 17/2.8. ROS 17/2.8 cells colonized and formed tumor nodules within one week in the lungs of nude mice. Whereas systemic delivery of Ad-RSV β Gal(recombinant adenoviral vector containing E. coli beta-galactosidase gene driven by a rous sarcoma virus universal promoter) resulted in non-specific expression of beta-glactosidase (β-gal) activity in the lung parenchyma, Ad-OC-β Gal administration resulted in specific β-gal expression in tumor cells deposited in the lung. When nude mice bearing ROS 17/2.8 lung tumors were treated with systemic Ad-OC-TK through tail vein administration, subsequent intra peritoneal ACV treatment significantly decreased the number of tumor nodules ($p<0.0001$) and the net lung wet weight ($p=0.0005$), and increased significantly ($0.005<p<0.01$) the survival of animals when compared to untreated and Ad-OC-TK or ACV-treated control groups. These results suggest that Ad-OC-TK plus ACV may be used as a systemic therapy for the treatment of osteosarcoma lung metastasis.

The osteocalcin promoter, and therapeutic agent of this and the parent application, Ad-OC-TK, is not limited to the delivery of therapeutic genes for treatment of tumors. This system is also adapted for the treatment of normal tissue. Co-administration, systemically or locally, of Ad-OC-TK with acyclovir (ACV) may be effective in treating benign prostatic hypertrophy, as well as arteriosclerosis.

BRIEF DESCRIPTION OF THE FIGURES

FIG. 1 is a reproduction of H. and E. staining (FIG. 1A) or immunohistostaining (1B, 1C and 1D) of lung tissue of nude mice receiving Ad-OC-B gal. The mice bore osteosarcoma lung metastases. FIG. 1B represents a control.

FIGS. 2(a–d) is a reproduction of stained tissue processed as described for FIG. 1, 25 days after tumor cell inoculation with the selected agent.

FIG. 3 graphically depicts reduction in the number of metastatic nodules in treated mice.

FIG. 4 graphically depicts the reduction in lung weight of treated animals.

FIG. 5 is a photo reproduction of stained tissue samples showing a reduction in tumor nodule size in treated mice. FIG. 1A reflects a control.

FIG. 6 is a graphic comparison of the survival rates of treated and non-treated mice.

FIG. 7 is a graphic comparison of body and prostate weight in normal intact rats, for both controls and treated rats.

DETAILED DESCRIPTION OF THE INVENTION

Figure 1:
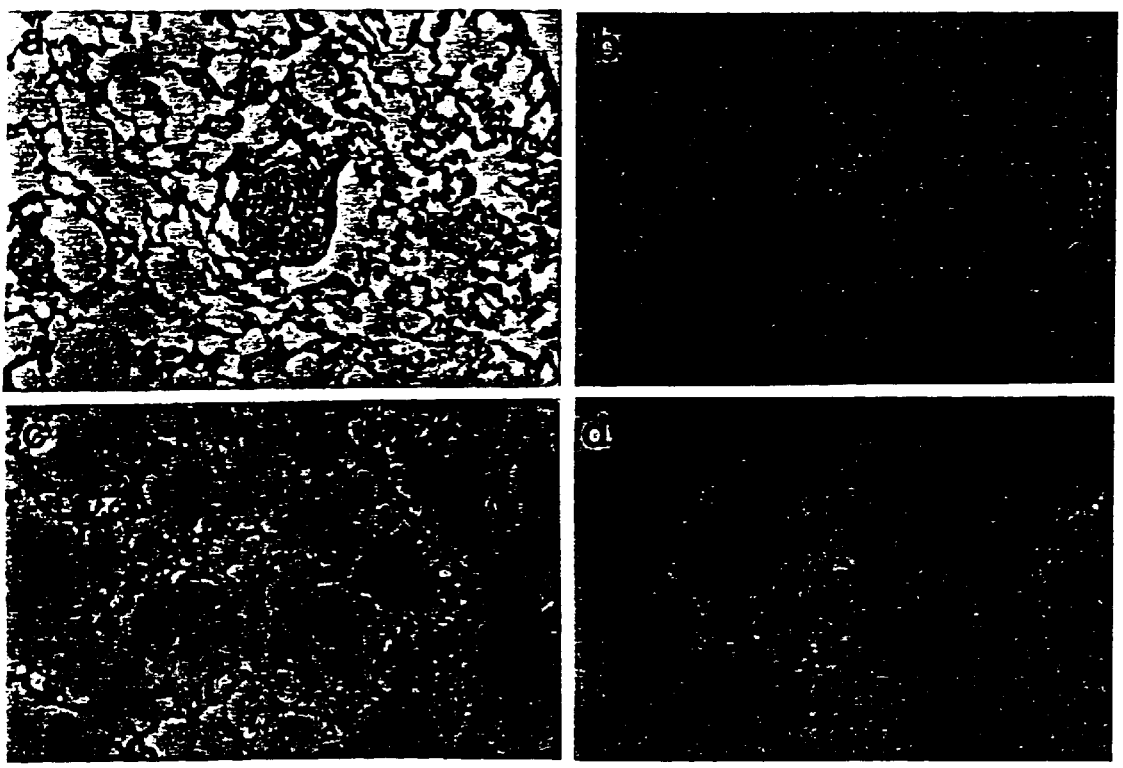
FIGS. 1–7 are provided herewith to augment the reader's understanding. They are not essential for understanding, and are described in greater detail, below.

As noted, this invention pertains to the systemic treatment of metastatic cancers, including osteosarcoma, prostate cancer, breast cancer, ocular melanoma, brain tumors and other tumors that metastasize to the lung or skeleton. Additionally, this invention finds application to the treatment of benign but nonetheless serious and life threatening conditions such as BPH and arteriosclerosis. These applications of this invention are discussed below, first in terms of treatment of metastatic cancers and then in terms of treatment of other tissues. There remains, however, a single modality of treatment common to all these applications—the systemic administration of Ad-OC-TK.

Metastatic Cancer Treatment

Materials and Methods

Cells and Cell Culture

ROS 17/2.8, a rat osteoblastic osteosarcoma cell line, was generously provided by Dr. Cindy Farrach-Carson (The University of Texas Dental Branch, Houston, Tex.). ROS 17/2.8 cells were cultured in Dulbecco's modified Eagle's medium (DMEM, GIBCO BRL, Grand Island, N.Y.) supplemented with penicillin (100 units/ml), streptomycin (100 mg/ml), and 10% fetal bovine serum (FBS) (Sigma Chemical Co., St. Louis, Mo.). The cells were fed three times a week with fresh growth media.

Construction and Preparation of Recombinant Adenoviral (Ad) Vectors

The construction of recombinant Ad vector containing OC promoter-TK (Ad-OC-TK) was described previously.[4] The recombinant OC promoter-β glactosidase (Ad-OC-β gal) or RSV (Rous Sarcoma virus) promoter-β glactosidase (Ad-RSV-β gal) was constructed similarly to Ad-OC-TK using the same protocol. Briefly, OC or RSV promoter plus $E.$ $coli$ β glactosidase (lacZ) gene and the polyadenylation signal from simian virus 40 were cloned first into a plasmid pΔE1sp1A (a gift from Dr. Frank Graham, McMaster University, Hamilton, Ontario, Canada), to generate the shuttle vectors, pΔE1sp1A-OC-β gal or pΔE1sp1A-RSV-β gal, respectively. The replication-defective adenovirus, Ad-OC-β gal and Ad-RSV-β gal were produced by cotransfecting pΔE1sp1A-OC-β gal or pΔE1sp1A-RSV-β gal with a recombinant adenoviral vector pJM17 into 293 cells using a DOTAP (Boehringer Mannheim Biochemicals) mediated transfection method.[16] The cell lysates were prepared from dishes that showed the cytopathic effect of adenovirus infection. A PCR analysis was conducted to identify the recombinant as well as the wild-type adenoviruses.[6] Recombinant adenoviruses were propagated in 293 cells and purified by the CsCl centrifugation method.[17] the purified virus stock was then dialyzed against 10 mM Tris buffer pH 7.5 containing 1 mM $MgCl_2$ and 10% glycerol. The plaque-forming unit (PFU) of the viruses was measured by a standard biologic plaque forming assay and OD measurements.[17]

Animal Model of Osteosarcoma Pulmonary Metastasis

Athymic Balb/c (nu/nu) mice at 5 to 6 weeks were purchased from Harlan Co. (Houston, Tex.). Tail vein injection of $5 \times 10^5$-ROS 17/2.8 cells in 50 μl of culture medium resulted in 100% histological incidence of pulmonary metastasis at 7 days (n-8, data not shown). All mice were maintained in facilities approved by the American Association of Accreditation of Laboratory Animal Care, and all animal studies were conducted in accordance with the principles and procedures outlined in the NIH Guide for the Care and Use of Laboratory Animals.

Immunohistochemical Staining

The removed lung tissues were fixed in 4% buffered formaldehyde, embedded in a paraffin block, and then sectioned. Tissue sections were deparaffinized, treated with 3% hydrogen peroxide ($H_2O_2$) and blocked with Super Block (Scytek Laboratories, Logan, Utah). To detect the expression of bacterial β-glactosidase, tissue sections previously blocked with Super Block were incubated with either 1:1000 diluted rabbit anti-$E.$ $Coli$ β gal polyclonal antibodies (5 prime-3 prime, Inc., Boulder, Colo.) or control rabbit serum at 4° C. for 24 hrs. Tissue sections were washed thoroughly and incubated for 1 hour with biotinylated goat anti-immunoglobulin antibody (Multilink) followed by 1 hour incubation with peroxidase-conjugated streptavidin (Label, BioGenex Laboratories, San Ramo, Calif.) at room temperature. Finally, the tissue sections were incubated with the substrate 3-amino-9-ethylcarbazole (AEC) for color development.

Treatment of Pulmonary Metastasis by Ad-OC-TK

The osteosarcoma pulmonary metastasis model was established as described above. Ad-OC-TK ($5 \times 10^8$ PFU per 50 μl) was injected via tail vein twice, at day 7 and 14, after ROS 17/2.8 injection. Daily acyclovir intra peritoneal administration (40 mg/kg body weight) started at day 6 after ROS 17/2.8 tumor cell inoculation and continued for 15 days. All animals were sacrificed and examined on day 25. The lungs were removed, photographed, and weighed, and the metastatic deposits were observed under a low-powered (20×) stereo microscope. Histomorphologic observations were made in all specimens according to a standard procedure. Student's t-test was employed to analyze the statistical significance of differences among control and treatment groups.

Long Term Survival Study

The end-points of the long term survival study are: animal death or sacrifice upon request by animal care takers because of excessive tumor burden causing animal distress, lethargy, ruffled fur or weight loss. The survival rate of the animals was analyzed by the Kaplan-Meier survival curve. The statistical significance of this study was analyzed with the generalized Wilcoxon test.[18]

Results

Establishment of Osteosarcoma Lung Metastasis

The ability of ROS 17/2.8 cells to colonize and form tumors in the lungs of nude mice was tested by injection of cells directly into the tail vein. Two inoculating cell numbers, $5 \times 10^5$ and $1 \times 10^6$ cells, were selected for intravenous administration via tail vein to mice. Tumor nodules were found in the lungs of all animals within one week (4 animals per group). Lung metastases appeared to be specific because on complete necropsy no other organs were found to harbor gross tumor mass. An additional forty-six animals studied subsequently demonstrated pulmonary metastasis on exploration at various time points beyond one week.

Specific Targeting of Osteosarcoma Lung Metastasis with Intravenous Osteocalcin Promoter-Driven Gene Therapy In order to test whether the OC promoter can mediate gene expression in normal lung cells, we constructed Ad-OC-β gal and Ad-RSV-β gal with transcriptional control of the β gal gene expression under the OC promoter and the universal promoter from Rous Sarcoma virus (RSV), respectively. Ad-OC-β gal ($1 \times 10^9$ PFU in 50 μl), Ad-RSV-β gal ($1 \times 10^9$ PFU in 50 μl of phosphate buffered saline (PBS) as a control was injected via tail vein of mice 7 days after ROS 17/2.8 cells injection. Mice were sacrificed and the lungs were removed for further analysis 48 hours after a single tail vein injection. The expression of β gal in the lung tissue and tumor nodules was detected by immunohistochemical staining with anti-bacterial β gal antibody.

In the Ad-RSV-β gal treated mice, the anti-β gal immunoreactivity was observed in both osteosarcoma lung metastases and normal lung tissue (FIG. 1c). Conversely, in the Ad-OC-β gal treated mice, the anti-β gal immunoreactivity was detected primarily in osteosarcoma lung metastases and not in normal lung tissue (FIG. 1d). No anti-β gal immunoreactivity was observed in the PBS treated host (FIG. 1b). These results demonstrate that OC promoter-mediated gene expression is localized preferentially in osteosarcoma tumors deposited in the lung but not in normal lung tissues.

Suppression of Osteosarcoma Lung Metastasis with Intravenous Ad-OC-TK Gene Therapy We next tested the therapeutic efficacy of intravenous Ad-OC-TK gene therapy for the treatment of osteosarcoma lung metastases. Twenty mice bearing ROS 17/2.8 tumor lung metastases were treated with either PBS (control), Ad-OC-TK alone, ACV alone, or Ad-OC-TK plus ACV. Animals were sacrificed and analyzed on day 25 after ROS 17/2.8 inoculation. Tumor nodules on the lung surface were counted with stereo-optic magnification and the lung wet weights were measured, and all the lung specimens were subjected to histological analysis.

Figure 3:
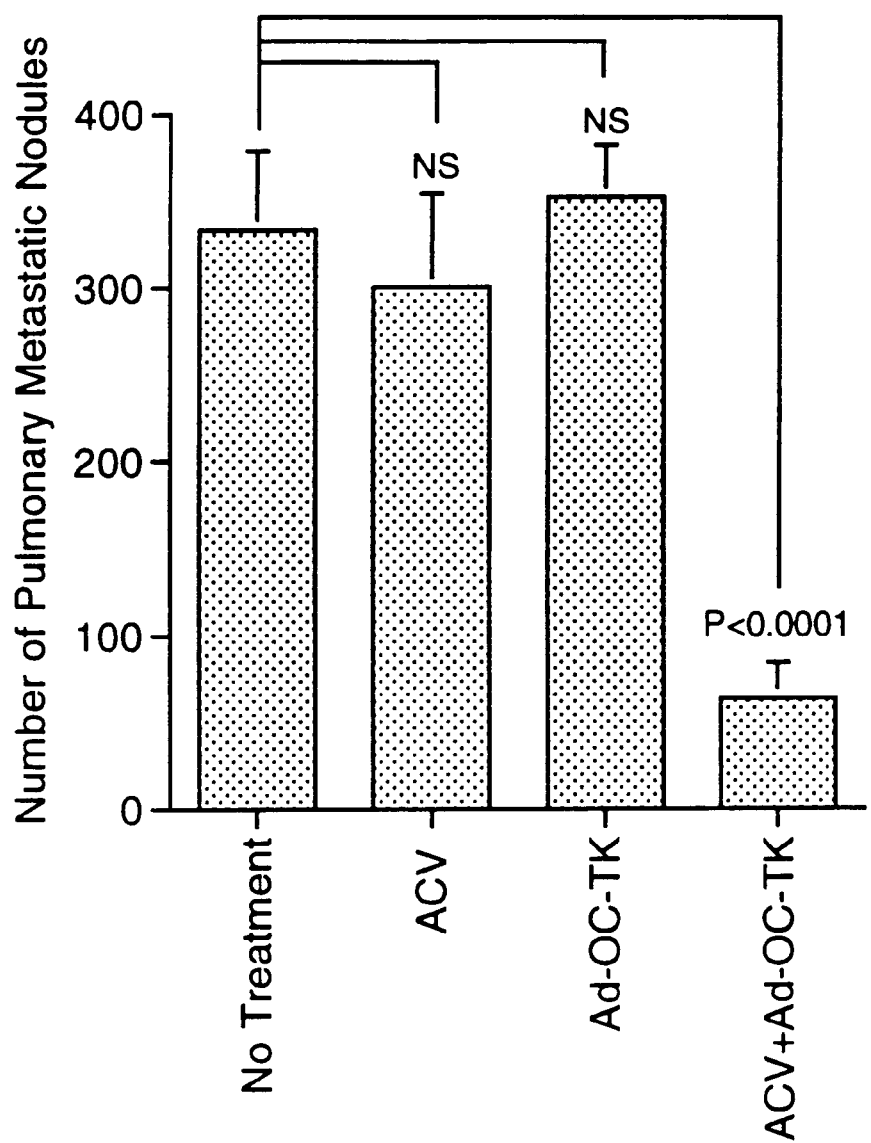
Figure 4:
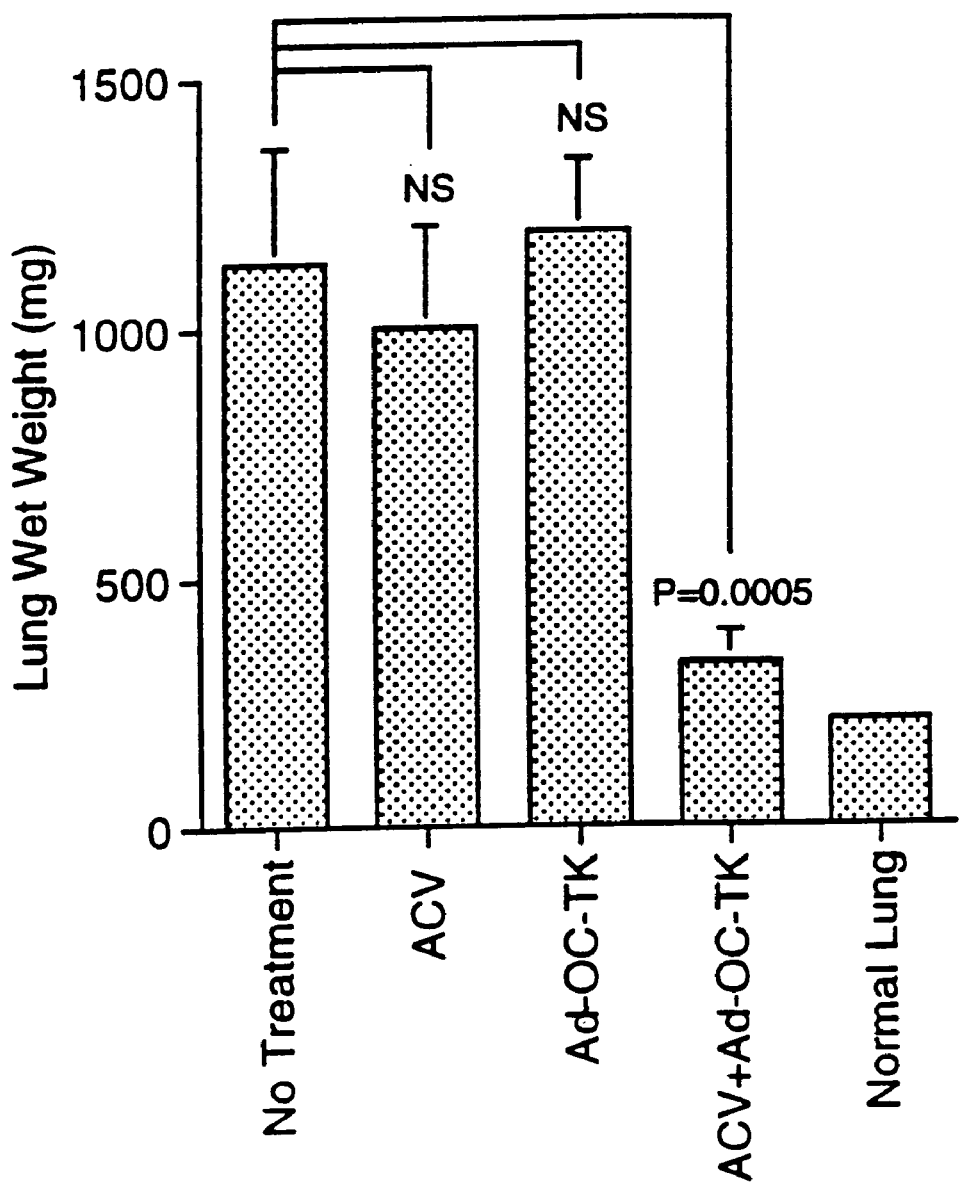

Grossly, metastatic lung nodules were observed on the lung surfaces in all of the animals (FIGS. 2a–d). In the Ad-OC-TK plus ACV treated group, both the number of nodules ($p<0.0001$) and the lung wet weight ($p=0.0005$) were significantly lower than in the PBS-treated control group (FIGS. 3,4). Histologically, osteosarcoma pulmonary metastases were identified in the lung tissue of all twenty animals. No statistical difference was demonstrated in either the number or the size of pulmonary metastases in the PBS, Ad-OC-TK alone, or ACV alone control groups. In comparison to PBS-treated specimens (FIG. 5a), the tumors in animals treated with Ad-OC-TK and ACV had a marked decrease in tumor size and demonstrated extensive necrosis (See FIG. 5b arrows).

Prolonged Survival with Ad-OC-TK Gene Therapy

Figure 6:
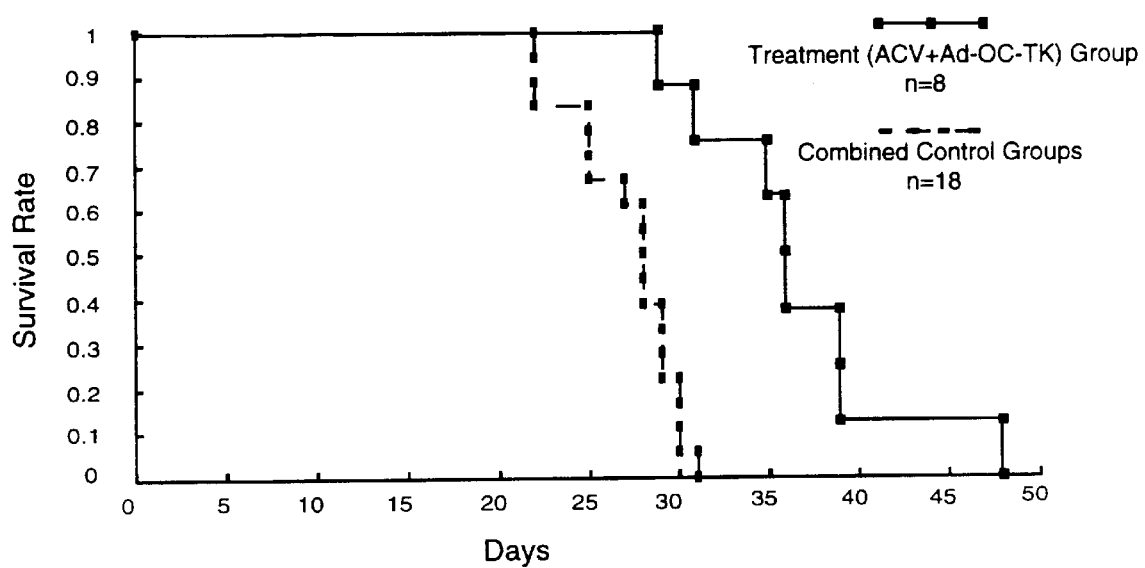
Figure 7:
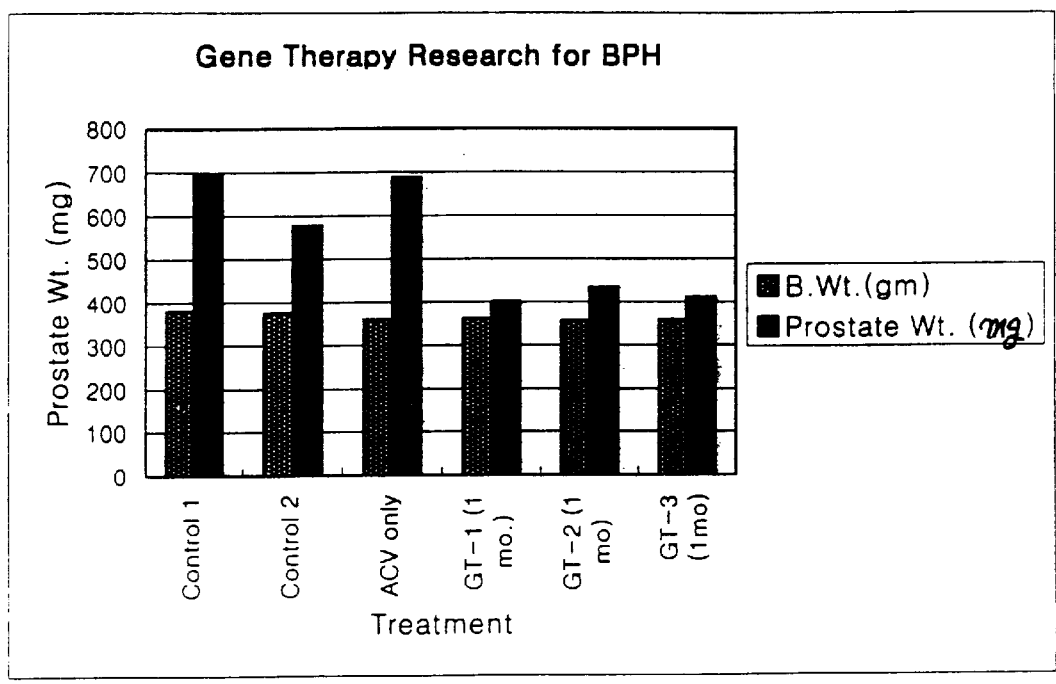

Twenty-six mice were inoculated with ROS 17/2.8 tumor cells as described above. Animals received either PBS, Ad-OC-TK alone, ACV alone, or Ad-OC-TK plus ACV and survivals were compared. No obvious difference in survival was detected among 3 control groups: PBS, Ad-OC-TK alone, or ACV alone. The survival of Ad-OC-TK plus ACV treated group, however, was significantly ($0.005<p<0.01$, generalized Wilcoxon test) prolonged. Mean survival time was $27.1\pm2.9$ days for the control animals and $36.6\pm5.8$ days for the Ad-OC-TK plus ACV-treated animals (FIG. 6).

Discussion

Since lung epithelium contains the first capillary bed encountered by therapeutic agents given systemically, several investigators have explored the use of a venous system to deliver therapeutic genes to the lung by cationic liposomes[7] [19–21] or retroviral vectors.[8] This application describes a new treatment strategy to target pulmonary metastases using a tumor-specific osteocalcin promoter-based toxic gene therapy given via a systemic route. We have shown recently that intratumoral injection of Ad-OC-TK to both human and rat osteosarcoma tumors grown at subcutaneous sites, significantly impaired tumor growth in vitro and in vivo. Moreover, we noted that combined administration of Ad-OC-TK/ACV plus methotrexate improved further the therapeutic efficacy of gene therapy for osteosarcoma cell growth both in vitro and in vivo. These results are set forth in parent U.S. patent application Ser. No. 08/785, 088 (now U.S. Pat. No. 5,772,993). Since osteosarcoma metastasises primarily to the lung, and lung vasculature is considered as the first major capillary bed that a systemically-given therapeutic agent encounters, we designed a strategy to target osteosarcoma pulmonary metastasis by the administration of Ad-OC-TK/ACV in an animal model. β-glactosidase reporter gene expression under the transcriptional control of the osteocalcin promoter is specifically expressed in osteosarcoma cells rather than normal lung parenchyma. In comparison to control animals, systemically delivered Ad-OC-TK plus ACV (via intravenous route) significantly retarded the growth of osteosarcoma pulmonary metastases and improved survival of treated animals.

While a limited number of tumor cells in the lung may be infected by Ad-OC-TK, as judged by the immunostaining of a comparable virus, Ad-OC-β gal (FIG. 1d), a surprisingly potent growth-inhibiting effect by Ad-OC-TK/ACV was noted in osteosarcoma lung metastases. This biologic effect is most likely derived from the existence of close gap junctions between osteosarcoma cells[22] which allows the phosphorylated form of ACV to exert its full bystander effect.

The observation that Ad-OC-TK/ACV delivered by an intravascular route effectively inhibited the growth of osteosarcoma lung metastases raises the question of delivering therapeutic viruses via local regional perfusion. For example, employing a Swan-Ganz type catheter may achieve improved local delivery. Isolated single-lung-perfusion technique for the chemotherapy of lung metastasis has increased the concentration of chemotherapeutic agents in human lung by 10–20 fold.[23] This technique offers promise for the delivery of Ad-OC-TK and subsequent treatment of osteosarcoma lung metastasis through systemic administration of ACV. The loco-regional delivery of gene therapy can achieve higher local viral concentration and infectivity, and reduce viral leakage systemically. It is also expected that this route of gene therapy delivery will avoid the interference of neutralizing antibody which can be flushed out of lung circulation prior to adenovirus administration. We are currently developing this loco-regional technique for the treatment of osteosarcoma pulmonary metastasis using a larger size of animal model (e.g. nude rate) in our laboratory.

In summary, we have shown for the first time that recombinant adenovirus can be given systemically to achieve a therapeutic effect on osteosarcoma lung metastasis. Ad-OC-TK/ACV dramatically inhibited the growth of lung nodules and significantly increased the survival of animals bearing osteosarcoma pulmonary metastases. This approach will open new avenues for targeting pulmonary metastasis using tissue-specific or tumor-specific promoters to guide the expression of therapeutic genes.

Systemic Treatment of Benign Conditions

The therapeutic agent that is the subject of this application, Ad-OC-TK is not limited in its uses to the treatment of cancer. A variety of benign conditions can also be addressed by the systemic administration of Ad-OC-TK, alone, or in combination with acyclovir (ACV). These conditions include benign prostatic hypertrophy and arteriosclerosis.

Benign prostatic hypertrophy (BPH) is a nearly universally observed symptom of aging in mammalian males, including humans. The enhanced growth of the prostate gland observed in this syndrome can be controlled by administration of Ad-OC-TK. Following the protocols set forth above normal male rats were collected and received therapeutically effective amount of Ad-OC-TK and ACV. Controls received placebo, or ACV alone. The rats receiving the treatment, Ad-OC-TK $5\times10^8$ PFU (50 μl of $1\times10^{10}$ PFU/ml stock) and ACV (14 days intraperatenial injection) showed a positive response in terms of inhibition of growth of the prostate gland. All animals were sacrificed after one month of treatment and began the program with an average body weight of 300 grams. Importantly, while prostate growth was inhibited, body weight values did not differ significantly. Clearly, administration of Ad-OC-TK in any sort of pharmaceutically effective carrier, particularly administered systemically, i.e., intravascularly, is effective in treating mammalian, including human, BPH.

This is confirmed by findings which demonstrate that Ad-OC-β-glactosidase and Ad-CMV-β-glactosidase are principally expressed in cultured primary human prostate cells derived from a BPH specimen, confirming effective delivery of this gene therapy region.

Arteriosclerosis is accompanied by the formation of arteriosclerotic plaques surrounding effective blood vessels. Osteocalcin expression is increased in these plaques. Frequently, the over expression of OC in these tissues is associated with increased calcium deposition. Jie et al., Calcified Tissue Intl. 59:352–356 (1996) and Jie et al., Atherosclerosis 116:117–123 (1995). See also Balica et al., Circulation 95:1954–1960 (1997). The over expression of OC, and accompanying calcium deposition, around the arteriosclerotic plaques formed lends itself to Ad-OC-TK-mediated gene therapy. The combined administration of this therapeutic agent, optionally coupled with the administration of ACV, offers gene therapy for actual regression of arteriosclerotic plaque, and effective treatment of arteriosclerosis.

A more detailed understanding of FIGS. 1–7 may be had by reference to the following figure legends.

FIG. 1. Tissue specific targeting of osteosarcoma lung metastasis with Ad-OC-β gal. PBS (50 µl), Ad-OC-β gal ($1 \times 10^9$ PFU per 50 µl) or Ad-RSV-β gal ( $1 \times 10^9$ PFU per 50 µl) was injected via the tail vein of a nude mice bearing osteosarcoma lung metastases to study tissue specific activity of OC promoter in lung environment. Animals were sacrificed two days after virus inoculation. Lungs were removed and processed for H. and E. staining (a) or immunohistostaining with anti-β gal antibody (b, c and d). H. and E. staining showed the presence of osteosarcoma lung metastasis (a). Control animals received PBS alone and did not show brown positive stain with anti-β gal antibody (b). Animals receiving Ad-RSV-β gal had β gal expression in both lung tissue and tumor nodules (c). Animals receiving Ad-OC-β gal expressed β gal only in tumors but not normal lung tissue (d). All tissue sections were photographed at high power.

Figure 2:
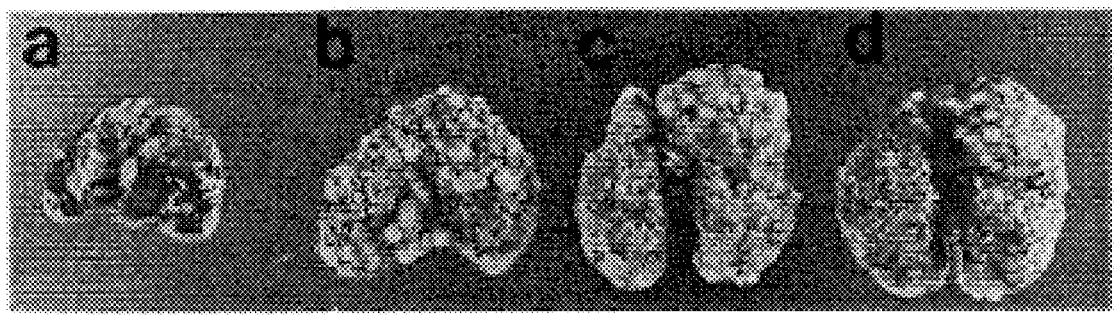

FIG. 2. Therapeutic effect of Ad-OC-TK/ACV. Animals bearing osteosarcoma lung metastases were treated with Ad-OC-TK/ACV (a), PBS (b), Ad-OC-TK (c), or ACV (d) treatment as described above. Animals were sacrificed 25 days after tumor cell inoculation, and the lungs were removed for analysis. Note that fewer pulmonary metastatic nodules were found on the lung surface of animals with Ad-OC-TK/ACV treatment (a) than in control animals with other treatments (b, c, d).

FIG. 3. Reduction of the number of pulmonary metastatic nodules with Ad-OC-TK/ACV treatment. Animals bearing osteosarcoma lung metastases were treated with PBS, ACV, Ad-OC-TK, or Ad-OC-TK/ACV as described above. Animals were sacrificed 25 days after tumor cell inoculation, and the lungs were removed for analysis. Animals receiving Ad-OC-TK/ACV treatment had significantly fewer lung tumor nodules compared to animals with other treatments ($p<0.0001$, t-test). There were no significant differences in the number of lung tumor nodules between receiving PBS, ACV, or Ad-OC-TK treatment.

FIG. 4. Reduction of the wet weight of lung carrying osteosarcoma tumor nodules with Ad-OC-TK/ACV treatment. Animals bearing osteosarcoma lung metastases were treated with PBS, ACV, Ad-OC-TK, or Ad-OC-TK/ACV as described above. Animals were sacrificed 25 days after tumor cell inoculation, and the lungs were removed for analysis. Animals receiving Ad-OC-TK/ACV treatment had significantly lighter lungs compared to those animals with other treatments ($p=0.0005$, t-test). There were no significant differences in lung wet weight between animals receiving PBS, ACV, or Ad-OC-TK treatment.

Figure 5:
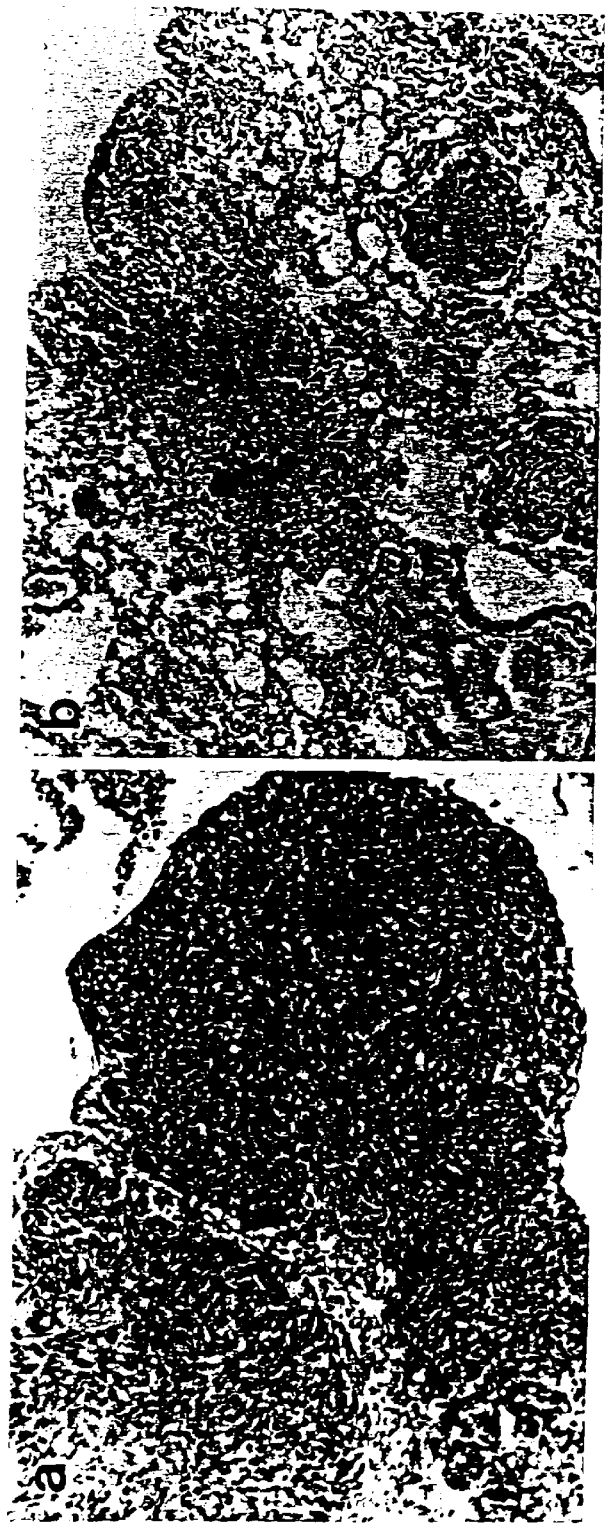

FIG. 5. Tumor regression induced by Ad-OC-TK/ACV. Animals bearing osteosarcoma lung metastases were treated with PBS, ACV, Ad-OC-TK, or Ad-OC-TK/ACV as described in Materials and Methods. Animals were sacrificed 25 days after tumor cell inoculation, and the lungs were removed for analysis. All of the nude mice with PBS, ACV, and Ad-OC-TK treatment had massive pulmonary metastatic tumor nodules (panel a, with PBS), but Ad-OC-TK/ACV treated animals had smaller tumor nodules (panel b) and extensive necrotic lesions (indicated by arrow) in the tumors. Tissue sections were photographed at low power.

FIG. 6. Survival of animals receiving Ad-OC-TK/ACV treatment. Animals bearing osteosarcoma lung metastases were treated with PBS (6 animals), ACV (6 animals), Ad-OC-TK (6 animals), or Ad-OC-TK/ACV (8 animals) as described above. The survival study end-points were animal death or sacrifice per request by animal care personnel for distress, as evidenced by lethargy, ruffled fur or weight loss. Since there were no significant differences between 3 control groups, animals receiving PBS, ACV, or Ad-OC-TK, these data were combined as control animals in the Kaplan-Meier survival rate study. The survival rate of Ad-OC-TK/ACV treated animals was significantly prolonged ($0.005<p<0.01$, generalized Wilcoxon test) when compared to the combined control animals.

REFERENCES

1. Cheon J, Ko S C, Gardner T A, et al. Chemogene therapy for osteosarcoma: Osteocalcin promoter-based suicide gene therapy in combination with methotrexate in a murine osteosarcoma model. *Cancer Gene Therapy*. 1997;4:359–365.
2. Bonnekoh B, Greenhalgh D A, Bundman D S, et al. Inhibition of melanoma growth by adenoviral-mediated HSV thymidine kinase gene transfer in vivo. *J Invest Dermatol*. 1995;104:313–317.
3. Eastham J A, Chen S H, Sehgal I, et al. Prostate cancer gene therapy: Herpes simplex virus thymidine kinase gene transduction followed by gancicrovir in mouse and human prostate cancer models. *Human Gene Therapy*. 1996;7:515–523.
4. Ko S C, Cheon J, Kao C, et al. Osteocalcin promoter-based toxic gene therapy for the treatment of osteosarcoma in experimental models. Cancer Research. 1996; 56:4614–4619.
5. Treat J, Kaiser L R, Sterman D H, et al. Treatment of advanced mesothelioma with the recombinant adenovirus H5.010RSVTK: a phase I trial (BB-IND 6274). *Human Gene Therapy*. 1996;7:2047–2057.
6. Eck S L, Alavi J B, Alavi A, et al. Treatment of advanced CNS malignancies with the recombinant adenovirus H5.010RSVTK: a phase I trial. *Human Gene Therapy*. 1996;7:1465–1482.
7. Lesoon-Wood L A, Kim W H, Kleinman H K, et al. Systemic gene therapy with p53 reduces growth and metastases of a malignant human breast cancer in nude mice. *Human Gene Therapy*. 1995;6:395–405.
8. Vile R G, Nelson J A, Casteleden S, et al. Systemic gene therapy of murine melanoma using tissue specific expression of the HSVtk gene involves an immune component. *Cancer Research*. 1994;54:6228–6234
9. Brand K, Arnold W, Bartels T, et al. Liver-associated toxicity of the HSV-tk/GCV approach and adenoviral vectors. *Cancer Gene Therapy*. 1997;4:9–16.
10. O'Reilly R. NCCN Pediatric osteosarcoma practice guidelines. *Oncology*. 1996; 10:1799–1806.
11. Saeter G, Hoie J, Stenwig A E, et al. Systematic relapse of patents with osteogenic sarcoma: Prognostic factors for long term survival. *Cancer*: 1995;75:1084–1093.
12. Naka T, Fukuda T, Shinohara N, et al. Osteosarcoma versus malignant fibrous histiocytoma of bone in patients older than 40 years. A clinicopathologic and immunohistochemical analysis with special reference to malignant fibrous histiocytoma-like osteosarcoma. *Cancer*. 1995;76:972–984.
13. Malawer M M, Link M P, Donaldson S S. Sarcomas of bone. In: DeVita J, V T, Hellman S, Rosenberg SA eds. *Cancer Principles and Practice of Oncology*, Philadelphia: J. B. Lippincott Company; 1993;1509–1566.
14. Ward W, Mikaelian K, Dorey F, et al. Pulmonary metastases of stage IIB extremity osteosarcoma and subsequent pulmonary metastases. *J. Clin. Oncol.* 1994; 12:1849–1858.
15. Ducy P, Karsenty G. Two distinct osteoblast-specific cis-acting elements control expression of a mouse osteocalcin gene. *Molecular and Cellular Biology*. 1995; 15:1858–1869.
16. Zhang W W, Fang X, D. B C, et al. Generation and identification of recombinant adenovirus by liposome-mediated transfection and PCR analysis. *Biotechniques*. 1993;15:868–872.
17. Graham F L, Provoke L. Methods for construction of adenovirus vectors. *Mol. Biotech*. 1995;3:207–220.
18. Wilcoxon F. Individual comparisons by ranking methods. *Biometrics Bull*. 1945; 1:80–83.
19. Zhu N, Liggitt D, Liu Y, et al. Systemic gene expression after intravenous DNA delivery into adult mice. *Science*. 1993;261:209–211.
20. Thierry A R, Lunardi-Iskandar Y, Bryant J L, et al. Systemic gene therapy: biodistribution and long-term expression of a transgenic in mice. *Proc. Natl. Acad. Sci. USA*. 1995;92:9742–9746.
21. Philip R, Liggitt D, Philip M, et al. In vivo gene delivery-efficient transfection of T-lymphocytes in adult mice. *J. Biol. Chem*. 1993;268:16087–16090.
22. Donahue H J, Mcleod K J, Rubin C T, et al. Cell-to-cell communication in osteoblastic networks: cell line-dependent hormonal regulation of gap junction function. *Journal of bone and mineral research*. 1995;10:881–889.
23. Weksler B, Lenert J, Ng B, et al. Isolated single lung perfusion with doxorubicin is effective in eradicating soft tissue sarcoma lung metastases in a rat model. *J Thorac Cardiovasc Surg*. 1994;107:50–54.

What is claimed is:

1. A method of inducing cytotoxicity in target cell of an individual in need of the same with a therapeutic agent comprising a recombinant adenovirus vector containing an osteocalcin promoter driven thymidine kinase (Ad-OC-TK) gene comprising administering said therapeutic agent in a pharmaceutically acceptable carrier to said individual intravascularly, in an amount effective to induce said cytotoxicity.

2. The method of claim 1, wherein said amount is effective to induce cytotoxicity in tumor cells.

3. The method of claim 2, wherein said tumor is a manifestation of a metastatic cancer.

4. The method of claim 3, wherein said metastatic cancer is osteosarcoma, breast cancer, prostate cancer, melanoma or brain tumor.

5. The method of claim 1, wherein said therapeutic agent is administered together with acyclovir.

6. A method of treating benign prostatic hypertrophy (BPH) in an individual in need of same, comprising administering Ad-OC-TK in a pharmaceutically acceptable carriers an amount effective to induce cytotoxicity in BAPH cells.

7. The method of claim 6, wherein said Ad-OC-TK is administered together with acyclovir.

8. The method of claim 6, wherein said Ad-OC-TK is administered intravascularly.

9. A method of treating arteriosclerosis in an individual in need of same, comprising administering Ad-OC-TK in an amount effective to induce regression of arteriosclerotic plaques.

10. The method of claim 9, wherein said Ad-OC-TK is administered, together with a pharmaceutically acceptable carrier, intravascularly.

* * * * *